United States Patent [19]
Tambo et al.

[11] Patent Number: 5,194,921
[45] Date of Patent: Mar. 16, 1993

[54] METHOD AND APPARATUS FOR DETECTING FLOCCULATION PROCESS OF COMPONENTS IN LIQUID

[75] Inventors: Norihito Tambo; Yoshihiko Matsui, both of Hokkaido; Tokio Ohto, Kawasaki; Yasushi Zaitsu, Kawasaki; Mutsuhisa Hiraoka, Kawasaki; Hiroshi Hoshikawa, Kawasaki; Haruo Ito, Kawasaki, all of Japan

[73] Assignee: Fuji Electric Co., Ltd., Kanagawa, Japan

[21] Appl. No.: 658,635

[22] Filed: Feb. 22, 1991

[30] Foreign Application Priority Data

Feb. 23, 1990 [JP] Japan ................................. 2-43064
Sep. 29, 1990 [JP] Japan ................................ 2-261771

[51] Int. Cl.⁵ .................... G01N 21/00; G01N 15/06
[52] U.S. Cl. .................................. 356/432; 356/436; 356/442; 250/573
[58] Field of Search ......................... 356/335-343, 356/435, 436, 432, 441, 442; 250/573, 574, 575

[56] References Cited

U.S. PATENT DOCUMENTS

| | | | |
|---|---|---|---|
| 4,077,724 | 3/1978 | Briggs | 356/442 |
| 4,136,959 | 1/1979 | Honkawa et al. | 356/436 |
| 4,348,112 | 9/1982 | Moreaud et al. | 356/343 |
| 4,843,247 | 6/1989 | Yamazoe et al. | 250/573 |
| 4,929,847 | 5/1990 | Yamazoe et al. | 356/436 |
| 4,950,908 | 8/1990 | Oblad et al. | 250/574 |

FOREIGN PATENT DOCUMENTS 0108605 5/1984 European Pat. Off. .
261839 11/1988 Fed. Rep. of Germany .

OTHER PUBLICATIONS

"Turbidity Fluctuations in Flowing Suspensions", Gregory Journal of Colloid and Interface Science, vol. 105, No. 2, Jun. 1985.
"Photometric Dispersion Analyser PDA 2000", Rank Brothers, Ltd.

Primary Examiner—Richard A. Rosenberger
Assistant Examiner—Hoa Q. Pham
Attorney, Agent, or Firm—Spencer, Frank & Schneider

[57] ABSTRACT

A sample flow, including a plurality of components which have different types of spectra and are subjected to flocculation, is irradiated with a light of beam including two or more wavelengths. The transmitted light beam is received by a photoelectric converting device, and electric signals corresponding to respective wavelengths of the transmitted light beam are obtained. The correlation coefficient between the electric signal is calculated, from which the flocculation process of the sample flow with regard to the elapsed time can be easily and quickly detected.

3 Claims, 7 Drawing Sheets

METHOD AND APPARATUS FOR DETECTING FLOCCULATION PROCESS OF COMPONENTS IN LIQUID

BACKGROUND OF THE INVENTION

1. Field of the Invention

The present invention relates to a method and apparatus for detecting, in a water purification process or the like, a flocculation process from flocculant components in a liquid after a flocculant is added into raw water including a plurality of components such as suspended particles or dissolved organic materials.

2. Description of the Prior Art

As is well known, raw water such as water from rivers, lakes and marshes takes a form of a suspension including a plurality of flocculated components. Here, the flocculated components refer to suspended components and dissolved components. A suspension, as is well known, refers to a liquid with suspended solid particles having diameters sufficient to cause light scatter. Suspended components refer to components existing in the raw water in the form of solid particles such as clay. Dissolved components refer to components uniformly mixed into the raw water, such as an acid like humic acid, an alkali, an inorganic salt, etc., and in particular, in this specification, it can refer to dissolved biologically metabolic organic compounds such as humic acid or fulvic acid.

By adding a flocculant into the raw water containing the above described components, these components are flocculated to form flocs. Removing the flocs from the raw water purifies the raw water.

When a flocculant is added into the raw water and stirred, the following components are formed in the flocculation process.

(i) Flocs B+X: When a flocculant is added to raw water, the flocculant is immediately hydrolyzed to form product X. At the same time, a dissolved component B is caught into the hydrolyzed product of flocculant X to form flocs B+X.

(ii) Compound A+B+X: A suspended component A in the raw water is captured into flocs B+X to form a compound (called hetero-flocs below) A+B+X.

(iii) Suspended components A which are not captured into the flocs A+B+X, exist independently in a manner similar to the situation in which no flocculant is added to the raw water.

(iv) Dissolved components B which are not captured into the flocs B+X and hetero-flocs A+B+X, and exist independently in a manner similar to the situation in which no flocculant is added to the raw water.

The flocs A+B+X are an object product of flocculation in water purification.

In this specification, the solid particles that come into existence in the flocculation process (i.e., the suspended components A, hydrolyzed product of flocculant X, flocs B+X, and hetero-flocs A+B+X) are called suspended particles.

The following four methods are known as conventional techniques for measuring concentration of suspended particles in a suspension.

(a) A first method obtains the concentration of suspended materials in a sample suspension (a uniform material layer) by Lambert-Beer's law representing the absorption of light when it passes through the uniform material layer, and a turbimeter using this method is also known. Lambert-Beer's Law can be expressed by the following equation (A).

$$-\ln T = KC \quad (A)$$

where
  T: transmittance ($I/I_0$);
    in which
      I: intensity of transmitted light;
      $I_0$: intensity of incident light;
  K: a constant determined by the type of suspended particles, a cross sectional area of incident light, and the path length of the incident light;
  C: concentration of the suspended particles.

According to equation (A), the concentration C of the suspended particles in the sample liquid can be found by knowing the light transmittance T of the sample liquid. The turbidimeter is arranged in such a way that it can be determined the concentration C by measuring the light transmittance T of the sample liquid and by applying equation (A) to the measured value.

(b) A second method determines the concentration of suspended particles in a sample liquid by measuring the number of particles in the liquid by using a laser. As means for measuring the number concentration of suspended particles in the liquid, the following counters are known: a particle counter that detects laser light scattered by particles; a particle counter based on a light obscuration method, which counts pulses to detect a reduction in the intensity of the transmitted light, this reduction being produced when a beam of light emitted from a laser or an LED passes the particles; and a Coulter counter that detects changes in electrical conductivity of the liquid produced when the particles pass through a pinhole.

(c) A third method is a variation of the first method in which the apparatus used is a kind of turbidimeter disclosed by John Gregory on pages 357-371 of Journal of Colloid and Interface Science, Vol. 105, No. 2, June 1985. This apparatus separates the DC component and AC component of the intensity of the transmitted light, and produces, as an output, a root means square value of the of the fluctuation of the light transmitted through the flowing particles. This makes it possible to calculate an average particle size for monodisperse suspension particles.

(d) A fourth method measures the concentration of soluble organic materials (biologically metabolic organic materials) represented by humin in raw water. Absorbance of ultraviolet light is used as a concentration index of the soluble organic materials (the biological metabolic organic materials). The absorbance of ultraviolet light (260 nm) can be measured by a spectrophotometer.

The information given by the above conventional means is limited to the average concentration of suspended particles in a suspension, particle-size distribution, absorbance, transmittance thereof, or the like. As a result, using the above means for measuring the suspension in the flocculation process in which the suspended particles are being aggregated by a flocculating agent added to the suspension, presents the following problems which will be explained corresponding to the above (a)-(d).

[a] The number concentration of suspended particles decreases as the aggregation proceeds, and at the same time, particle sizes grow larger. Thus, the two parameters (the number concentration and the particle sizes) change so as to cancel each other with regard to turbidity. As a result, it is difficult to obtain direct information about the flocculation process from the turbidimeter. In practice, the conditions for process control are judged by measuring the turbidity after the flocculation process has been completed. Accordingly, a quick feedback control is impossible because it takes a long time to obtain the result of the measurement of the flocculation process.

[b] In the particle counter, basically only one suspended particle is allowed to pass through the beam or pinhole at a time, which is difficult to satisfy because the concentration of the suspension which is treated in the flocculation process is high. Hence, the particles aggregate densely. Accordingly, measuring the concentration of the suspension when it is high using the particle counter requires dilution of the suspension to make a sample liquid. In addition, the information obtained by the particle counter is limited to the concentration of the suspended particles and to the particle-size distribution. Information regarding the flocs produced from the reaction between the flocculating agent and flocculated components cannot be obtained. Accordingly, the means of (b) above cannot detect the flocculation process of the flocculant components in the suspension.

[c] Turbidimetry can use a high concentration suspension without dilution because it measures statistical fluctuation amounts. The information regarding the flocs themselves, however, cannot be obtained by the measurement means.

[d] The means of (d) above determines the concentration of dissolved components from an absorbance measured by the spectrophotometer. Thus, the behavior of the flocculation process cannot be measured.

SUMMARY OF THE INVENTION

It is therefore an object of the present invention to provide a method and apparatus that can quickly measure a flocculation process which is initiated by adding a flocculant into a sample liquid including suspended components and dissolved components, and during which the plurality of components in the sample liquid are being aggregated into a plurality of flocs from the suspended components, dissolved components and the flocculant.

The inventors carried out the following experiment. First, a beam of light was preselected which included a plurality of wavelength components, and irradiated a sample liquid with the beam of light. The wavelength components were determined so that they exhibited a distinct or dominant absorption or scattering with regard to respective suspended components and flocculating components to be measured. Second, the transmitted beam of light (which corresponds to absorbances) through the sample liquid was measured so that transmitted light signals each corresponding to the principal absorption wavelength of each suspended particle in the sample liquid were measured. Finally, correlation coefficients between these light signals (i.e., absorbances) were calculated. This experiment showed that the correlation coefficients vary in accordance with the flocculation state of the components to be coagulated.

Consequently, the flocculation state of the plurality of components in the same liquid can be easily found by measuring the transmitted part of the light beam irradiating the sample liquid, and by calculating the correlation coefficients between the transmitted light signals or the absorbances by electronic circuitry using microcomputers.

On the other hand, the concentration change of the dissolved component that has not yet coagulated in the sample liquid plays an important role, as an index, of finding the process of purification of the sample liquid: this is because the removal efficiency of the dissolved component in the sample liquid can be found on the basis of the concentration change of the dissolved component that has not yet coagulated in the sample liquid; and the concentration of the uncoagulated dissolved component can be obtained from the absorbance of that component. Conventionally, the concentration of the uncoagulated dissolved component must be measured after preliminary processing wherein the suspended particles in the sample liquid are physically removed therefrom.

When the absorbances are measured while irradiating the sample liquid which flows through a flow cell with the beam of light including at least two wavelengths, deviation (fluctuated) values are obtained. The deviation takes place due to the flocculation of the plurality of components that have been uniformly dispersed in the sample liquid. In other words, the flocculation of the components means the spatial localization in the distribution of the components in the sample liquid, and the distribution probability of the flocs in the light path follows a Poisson distribution. The inventors of the present invention have found, on the basis of the above facts, that the absorbances (concentrations) of the uncoagulated dissolved components in the sample liquid can be accurately calculated by measuring deviations of the absorbances of the respective wavelengths, without the preliminary processing of removing the suspended particles in the sample liquid.

The present invention is carried out in view of the above considerations.

According to a first aspect of the present invention, there is provided a method for detecting a flocculation process with a plurality of components in a sample liquid, which is produced by adding a flocculant into the sample liquid including at least a suspended component and a dissolved component, the method comprises the steps of:

irradiating a flow of the sample liquid with a beam including at least first and second wavelength components having different wavelengths;

converting with an photoelectric converting means a transmitted beam, which is a part of the beam passing through a flow of the sample liquid, into electric signals each corresponding to the wavelength components; and calculating using the electric signals intensities of the wavelength components of the transmitted beam, mean values, standard deviations and coefficients of variation of absorbances of the wavelength components, and correlation coefficients between the intensities of the wavelength components of the transmitted beam.

Here, a first wavelength component may be selected so as to be absorbed only by the suspended component, the second wavelength components may be selected so as to be absorbed by both the suspended component and the dissolved component including the flocculant, and the step of calculating correlation coefficients may comprise the steps of:

calculating a mean value $\overline{E}_1$ of the absorbance of the first wavelength component;

calculating a standard deviation $E_{r1}$ of the absorbance of the first wavelength component;

calculating a mean value $\overline{E}_2$ of the absorbance of the second wavelength component;

calculating a standard deviation $E_{r2}$ of the absorbance of the second wavelength component;

calculating a time serial correlation coefficient $\rho_{12}$ between the absorbances of the first and second wavelength components; and calculating absorbance $E_2'$ of an uncoagulated dissolved component which is uniformly contained in the sample liquid without having been adsorbed by particles in the sample liquid by using the following equation (1) and the values $\overline{E}_1$, $E_{r1}$, $\overline{E}_2$, $E_{r2}$, and $\rho_{12}$.

$$E_2' = \overline{E}_2 - \frac{\overline{E}_1}{\rho 12} \cdot \frac{E_{r2}}{E_{r1}} \tag{1}$$

According to another aspect of the present invention, there is provided an apparatus for detecting a flocculation process of a plurality of components in a sample liquid, which is produced by adding a flocculant into the sample liquid including at least a suspended component and a dissolved component, the apparatus comprises:

a light source for emitting a beam of light including a plurality of wavelength components having different wavelengths;

a flow cell through which the sample liquid flows;

first optical means for transmitting the beam of light and for irradiating the flow cell;

photoelectric converting means for converting a transmitted beam, which is a part of the beam passing through the flow cell through which the sample liquid flows, into electric signals each corresponding to the wavelength components; and calculating means for calculating from the electric signals, intensities of the wavelength components of the transmitted beam, mean values, standard deviations and coefficients of variation of absorbances of the wavelength components, correlation coefficients between the intensities of the wavelength components of the transmitted beam.

The above and other objects, effects, features and advantages of the present invention will become more apparent from the following description of the embodiments thereof taken in conjunction with the accompanying drawings.

DETAILED DESCRIPTION OF PREFERRED EMBODIMENTS

Figure 1:
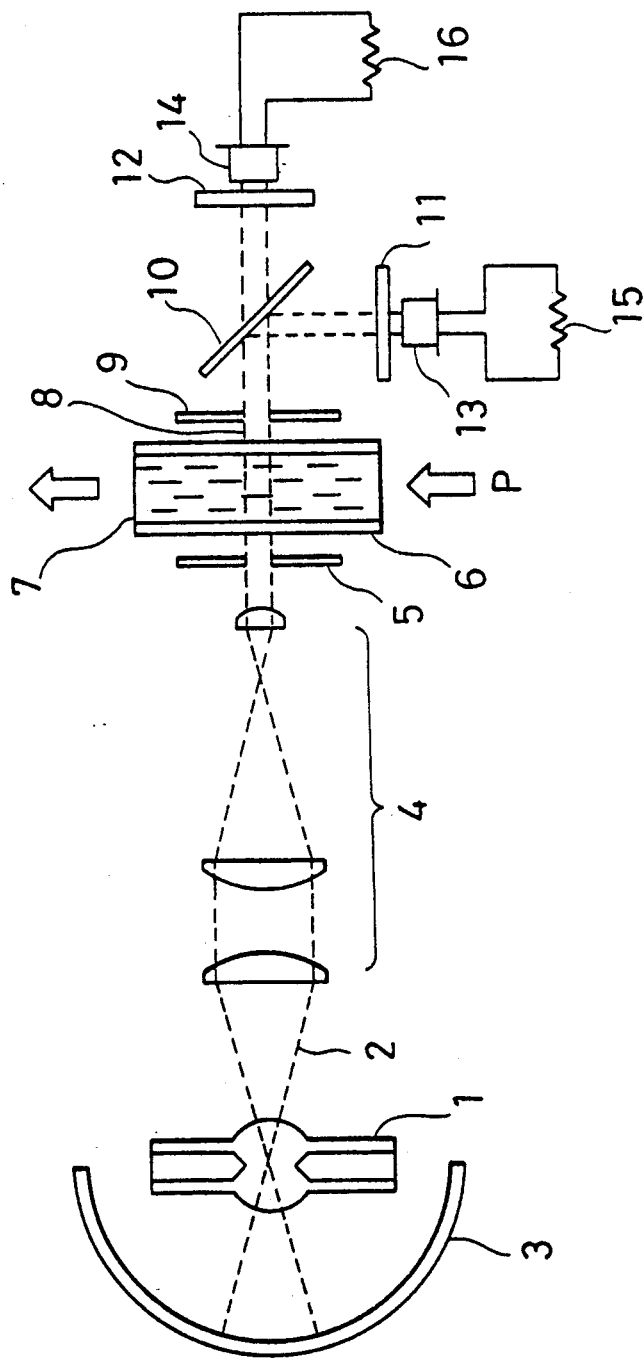
FIG. 1 is a schematic diagram showing an example of an optical system of the apparatus of the present invention.

The invention will now be described with reference to the accompanying drawings.

The present invention uses a beam of light including at least two wavelengths $\lambda_1$ and $\lambda_2$ which exhibit distinct or dominant absorption or scattering characteristics with regard to a suspended component and a flocculated component in a sample liquid. The beam of light irradiates the sample which includes a plurality of components to be flocculated. Then, the transmitted or absorbed amount of the wavelength components of $\lambda_1$ and $\lambda_2$ through the sample liquid are simultaneously measured so that a correlation coefficient between the two wavelength components of the transmitted beam is calculated in real time, thereby measuring the progress of the flocculation process.

As previously described, when a flocculant is added to raw water, the flocculant is immediately hydrolyzed to form product X. At the same time, a dissolved component B is caught into the hydrolyzed product of flocculant X to form flocs B+X. After that, a suspended component A in the raw water adheres to the flocs B+X to form a compound (hetero-flocs) A+B+X.

Accordingly, observing the flocculation process after a flocculant is added to raw water is to observe a simple flocculation system in which the two components, namely, a suspended component A which exists in the form of suspended particles, and flocs B+X coagulate into the final form of flocs A+B+X. In the later description in which the flocculation process is considered, the flocs are represented as a component M, the suspended component is represented as a component A, and the hetero-flocs A+B+X is referred to the flocs A+M.

Furthermore, the beam of light irradiating the sample liquid is selected to include two wavelengths $\lambda_1$ and $\lambda_2$: the wavelength $\lambda_1$ is absorbed only by the suspended component A; whereas the wavelength $\lambda_2$ is absorbed by both the suspended component A and the flocs B+X.

Let us consider the behavior of the absorbance of each wavelength under the conditions set in connection with the flocculation model and the wavelengths. It is obvious that fluctuation of the absorbances of respective wavelengths results from spatial localization (deviation) of the concentrations of the components in the liquid. The components A and M cause the fluctuation of the absorbances immediately after the addition of the flocculant and these components A and M are independent. Of these components, the component A absorbs both wavelengths $\lambda_1$ and $\lambda_2$, and hence the absorbances of the light components of both wavelengths simultaneously fluctuate when the component A passes across the path of the light beam. In contrast, when the component M passes across the path of the light beam, only the absorbance of the light component of wavelength $\lambda_2$ fluctuates. As a result, the correlation coefficient between the absorbances or the waveforms of the two wavelengths of the transmitted light beam is less than 1 in a period during which a sufficient number of the two components A and M randomly pass across the light path. As the flocculation proceeds, the component A+M increases, and so the concentrations of the components A and M which have been independently dispersed in the liquid decreases. When the component A+M passes the light path, both the absorbances of the wavelengths $\lambda_1$ and $\lambda_2$ simultaneously fluctuate, and the ratio of the magnitudes of the fluctuation is determined by the composition ratio of the components A and B in the component A+M. Thus, as the component A+M increases with the progress of the flocculation, the correlation coefficient increases, and finally, when the flocculation completes so that all suspended particles in the liquid have coagulated to the component A+M, the correlation coefficient becomes one.

The theoretical support of this is described hereinafter in Appendix 1.

On the other hand, the concentration change of the dissolved component B that has not yet coagulated in the sample liquid plays an important role, as an index, of finding the degree of purification of the sample liquid: this is because the removal efficiency of the dissolved component B in the sample liquid can be found on the basis of the concentration change of the dissolved component B that has not yet coagulated in the sample liquid.

As clearly seen, the concentration of the uncoagulated dissolved component B must be considered in a three component system including the dissolved component B: the system is considered wherein the suspended component A and the dissolved component B exist in the sample liquid, a flocculant added to the sample liquid is hydrolyzed to form product X, the dissolved component B is caught into the hydrolyzed product of flocculant X to form the flocs B+X, and the suspended component A in the raw water adheres to the flocs B+X to form the hetero-flocs A+B+X.

In this case, the absorbance of the uncoagulated dissolved component B can be obtained as follows: first, a part of the absorbance of the light of the wavelength $\lambda_2$ which results from the suspended particles, is expressed by a measurable statistic based on the fact that the number concentration of the suspended particles is proportional to the absorbance, and that the correlation coefficient indicates the flocculation state; and second, the absorbance resulting from the suspended particles is subtracted from the total absorbance of the wavelength $\lambda_2$, thereby obtaining the absorbance of the uncoagulated dissolved component B.

The following equation (1) can be induced from the above consideration, and the absorbance $E_2'$ of the uncoagulated dissolved component B can be calculated by electronic circuitry having microcomputers.

$$E_2' = \overline{E_2} - \frac{\overline{E_1}}{\rho_{12}} \cdot \frac{E_{r2}}{E_{r1}} \quad (1)$$

where:

$\overline{E_1}$ is the mean value of the absorbance of the light beam of wavelength $\lambda_1$;

$\overline{E_2}$ is the mean value of the absorbance of the light beam of wavelength $\lambda_2$;

$E_{r1}$ is a standard deviation of the absorbance $E_1$;

$E_{r2}$ is a standard deviation of the absorbance $E_2$; and $\rho_{12}$ is a time serial correlation coefficient between the absorbances of the wavelengths $\lambda_1$ and $\lambda_2$.

The removal efficiency by the coagulated dissolved component B is calculated by comparing the absorbance of the uncoagulated dissolved component B before and after the flocculation process.

The calculation method of the concentration of the uncoagulated dissolved component B is described hereinafter in Appendix 2.

Next, an apparatus to which the present invention is applied, and the operation thereof will be described.

FIG. 1 is a schematic diagram showing an optical system of the apparatus. In FIG. 1, an illumination beam of light 2 emitted from a xenon lamp 1 is condensed by a reflector 3, is incident to a collimator 4, is further shaped by a slit 5 into a beam having a predetermined cross-sectional shape, and is incident onto a sampling liquid 7 flowing in the direction indicated by an arrow P in a flow cell 6 made of fused quartz. A beam of light 8 transmitted through the sampling liquid 7 is passed through a slit 9 identical to slit 5, and is incident to a half mirror 10. The half mirror 10 splits the beam into two beams: one of the two beams is incident to a photodiode 13 through an interference filter 11; and the other beam is incident to a photodiode 14 through an interference filter 12. The photodiodes 13 and 14 produce voltage signals $V_1$ and $V_2$ across load resistors 15 and 16, respectively.

The apparatus of FIG. 1 produces two beams of different wavelengths to be observed by using the interference filters 11 and 12. This arrangement has an advantage that the configuration of the optical system and signal processing circuitry not shown in FIG. 1 can be made simple, although it has a disadvantage that the degree of freedom with regard to the selection of wavelengths is restricted.

Figure 2:
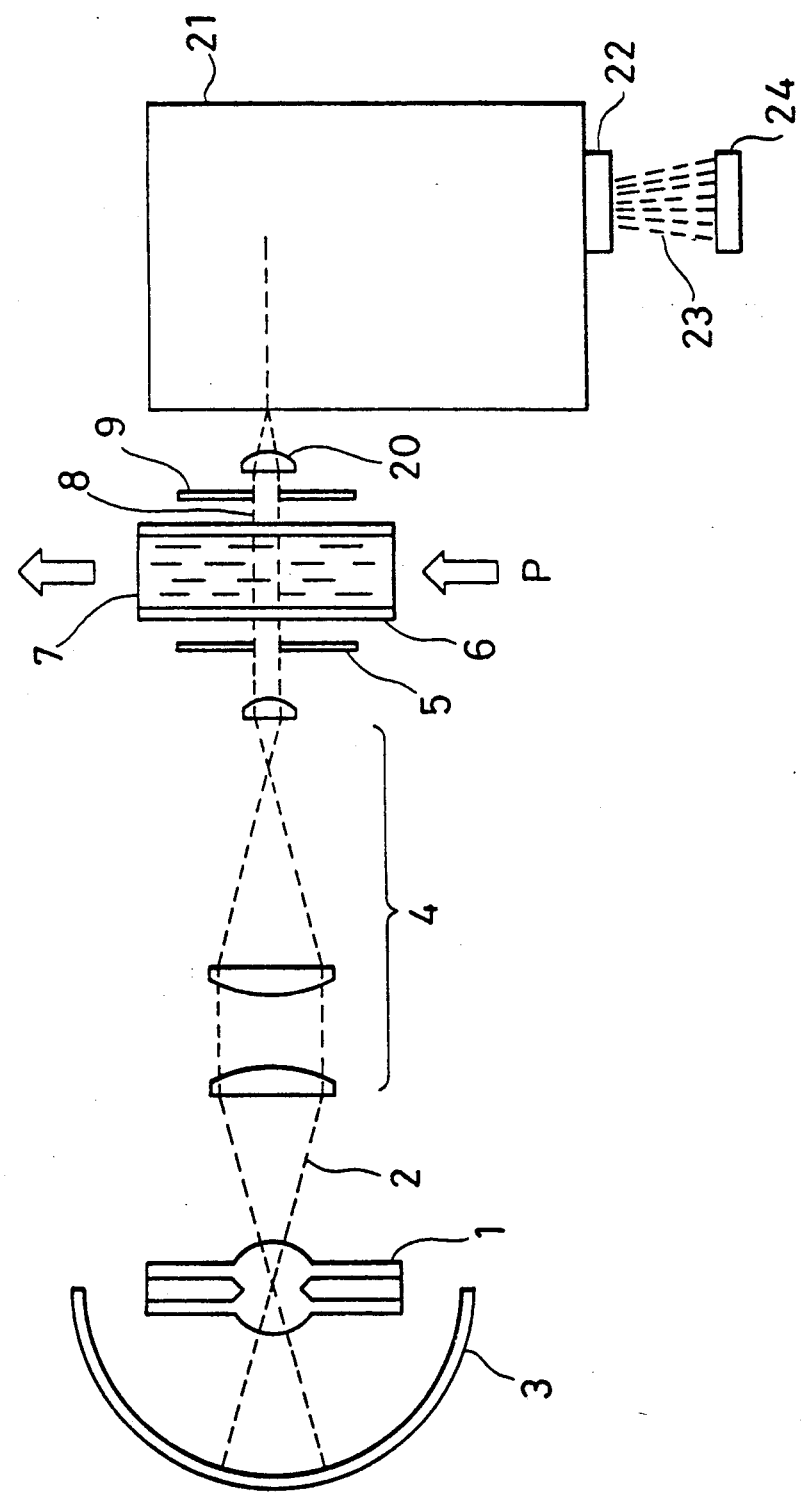
FIG. 2 is a schematic diagram showing another example of the optical system.

FIG. 2 is a schematic diagram showing another optical system of the apparatus employing a spectroscope 21 as a light receiving system. In FIGS. 1 and 2, like reference numerals designate like parts. This system in FIG. 2 uses condenser lens 20 instead of the half mirror 10 of FIG. 1 so as to make the light beam 8 enter the spectroscope 21 which produces spectrum 23 of the beam 8 at its outlet 22. The spectrum 23 is received by a photodiode array 24, and is converted into an electric signal.

The apparatus of FIG. 2 requires a means for calibrating the wavelength of the spectroscope 21, and a driver circuit (not shown) for driving the photodiode array 24, which makes the system more complicated as compared with the optical system in FIG. 1. This system, however, has an advantage that the selection of the wavelengths can be carried out more easily because the transmitted beam 8 is produced as the spectrum 23.

Next, the signal processing circuitry will be described by exemplifying the apparatus of FIG. 1.

Figure 3:
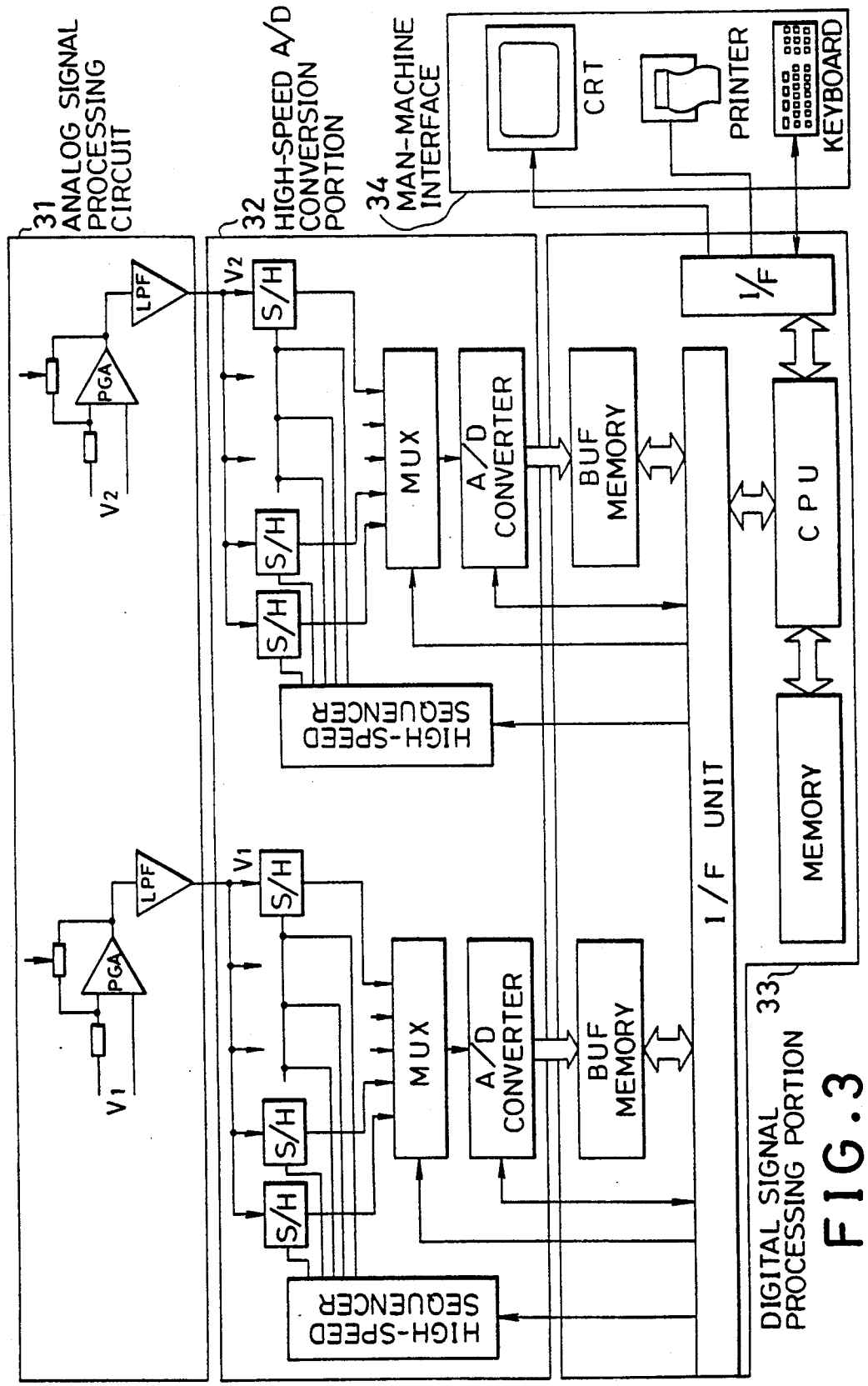
FIG. 3 is a block diagram showing a processing circuit of 2-wavelength transmitted optical signals obtained by the optical system of FIG. 1.

FIG. 3 is a block diagram showing a processing circuit of signals $V_1$ and $V_2$ corresponding to the two different wavelengths of the transmitted beam produced from the optical system of FIG. 1. In FIG. 3, the system is composed of the following elements: an analog signal processing circuit 31 comprising programmable gain amplifiers (PGA) and low-pass filters (LPF); a high-speed A/D conversion portion 32 comprising sample-and-hold circuits (S/H), multiplexers (MUX), and high-speed sequencers; a digital signal processing portion 33 comprising buffer memories, interfaces, a main memory and a CPU; and a man-machine interface 34 comprising a CRT, a printer, a keyboard, etc.

The analog signal processing circuit 31 amplifies the input signals $V_1$ and $V_2$ and reduces noises thereof to produce signals $V_1$ and $V_2$. The high-speed A/D converting portion 32 converts the signals $V_1$ and $V_2$ into digital signals. The digital signal processing portion 33 executes a programmed operation for the digital signals. The CRT or the printer displays the results of the operation. Various parameters necessary for the operation are entered from the keyboard to the CPU. Likewise, the operation of the entire system is controlled by entering necessary data from the keyboard to the CPU.

The procedure of the digital processing will be described in more detail.

The output signals $V_1$ and $V_2$ are simultaneously converted to the digital signals during one sampling time T, and are stored in the buffer memories as N-discrete data. The CPU immediately reads the converted data, and executes the following operation on the data.

$$\overline{x_i} = \left( \sum_{j=1}^{N} x_j \right)/N \tag{49}$$

$$x_{irms}^2 = \left( \sum_{j=1}^{N} x_j^2 \right)/N - \overline{x_i}^2 \tag{50}$$

$$\overline{x_{1i} \cdot x_{2i}} = \sum_{j=1}^{N} (x_{1j} - \overline{x_{1i}})(x_{2j} - \overline{x_{2i}})/N \tag{51}$$

When M-times of samplings have been completed, the CPU calculates the average of each series of data, and the correlation coefficient $\rho$ between the two series of data.

$$\overline{X} = \left( \sum_{i=1}^{M} \overline{x_i} \right)/M = \overline{V} \tag{52}$$

$$X_{rms} = \left( \sum_{i=1}^{N} x_{irms} \right)/M = V_{rms} \tag{53}$$

$$\overline{X_1 \cdot X_2} = \sum_{i=1}^{M} \overline{x_{1i} \cdot x_{2i}}/M = \overline{V_1 \cdot V_2} \tag{54}$$

$$\rho = \overline{X_1 \cdot X_2}/(X_{1rms} X_{2rms}) \tag{55}$$

Thus, the CPU calculates the correlation coefficient $\rho$, and outputs it to the CRT or the printer to display a graph or to print the data. The values of $\overline{V}_1$, $\overline{V}_2$, $V_{1rms}/\overline{V}_1$ and $V_{2rms}/\overline{V}_2$ are equal to the coefficients of variation obtained by the turbidity fluctuation measuring method mentioned before as a conventional method. Accordingly, the average particle size of the flocs can be calculated.

In addition, the statistic operation on the absorbance basis can be executed by performing logarithmic transformation for the two components of different wavelengths of the transmitted light beam. More specifically, the operation can be carried out by adding logarithmic transformation circuits as shown in FIG. 4 before the analog signal processing circuit 31 of FIG. 3.

Figure 4:
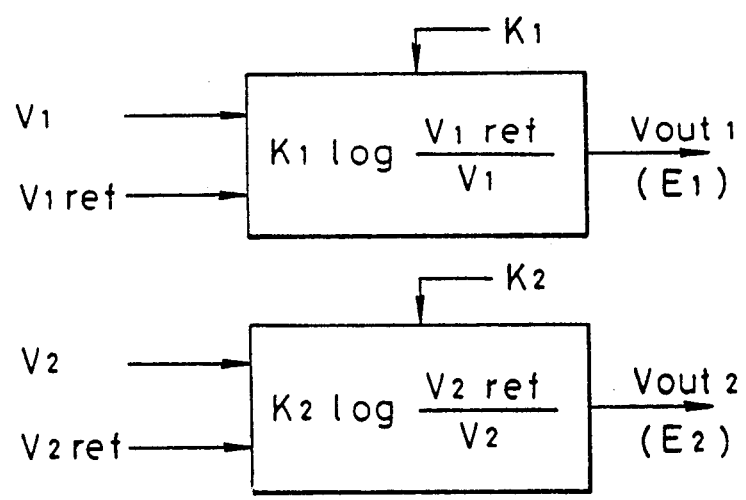
FIG. 4 is a block diagram showing a log-conversion circuit for converting the transmitted optical signals into absorbances.

In FIG. 4, $V_1$ and $V_2$ designate the components of wavelengths $\lambda_1$ and $\lambda_2$ of the light beam 8 transmitted through the flow cell 6, $V_{1ref}$ and $V_{2ref}$ designate reference signals which are directly fed from the light source 1 and are used to monitor the amounts of light, $V_{out1}$ and $V_{out2}$ denote output signals from the logarithmic transformation circuits, and $K_1$ and $K_2$ designate scale-factor signals which are set at 1 in this system for simplicity. The variation of the amount of light at respective wavelengths can be canceled by logarithmically transforming the ratios between the reference signal $V_{1ref}$ and the transmitted beam $V_1$, and between the reference signal $V_{2ref}$ and the transmitted beam $V_2$. The absorbances $E_1$ and $E_2$ of the sampling liquid can be calculated by the following equation by using the prestored logarithmically transformed signals obtained with regard to pure water when it was flowed through the flow cell 6.

$$E_i = \log \frac{V_{iref}}{V_i} - \log \frac{V_{iref}}{V_i^o} = \log \frac{V_i^o}{V_i} \tag{56}$$

where i=1 or 2 corresponding to the wavelengths $\lambda_1$ and $\lambda_2$, respectively.

The equation (49) is an equivalent of the equations (10) and (11) in the following Appendix 1. The logarithmic transformation thus performed makes it unnecessary to use an approximation as in the equation (12) in the following Appendix 1. The calculations according to the equations (49)-(55) enables the CPU to theoretically determine strict statistic quantities by using the absorbance values as variables X and x. Furthermore, using the absorbances as variables enables the CPU to calculate the absorbance $E_2'$ of the above-mentioned dissolved components that are not captured in flocs, and the removed ratios thereof by using the equations (44) and (48).

On the other hand, when only the correlation coefficient $\rho$ is necessary, it can be calculated with ease as follows: first, the direct current (DC) components of the signals obtained by photoelectrically converting the transmitted light 8 are eliminated by the alternating coupling so that the average values of the signals become zero; and second, the correlation coefficient can be calculated from the effective values (rms values) of the two signals, and the product of the two signals using the equation (19) in the following Appendix 1. Thus, the apparatus can be constructed by only a simple analog circuit as shown in FIG. 5.

Figure 5:
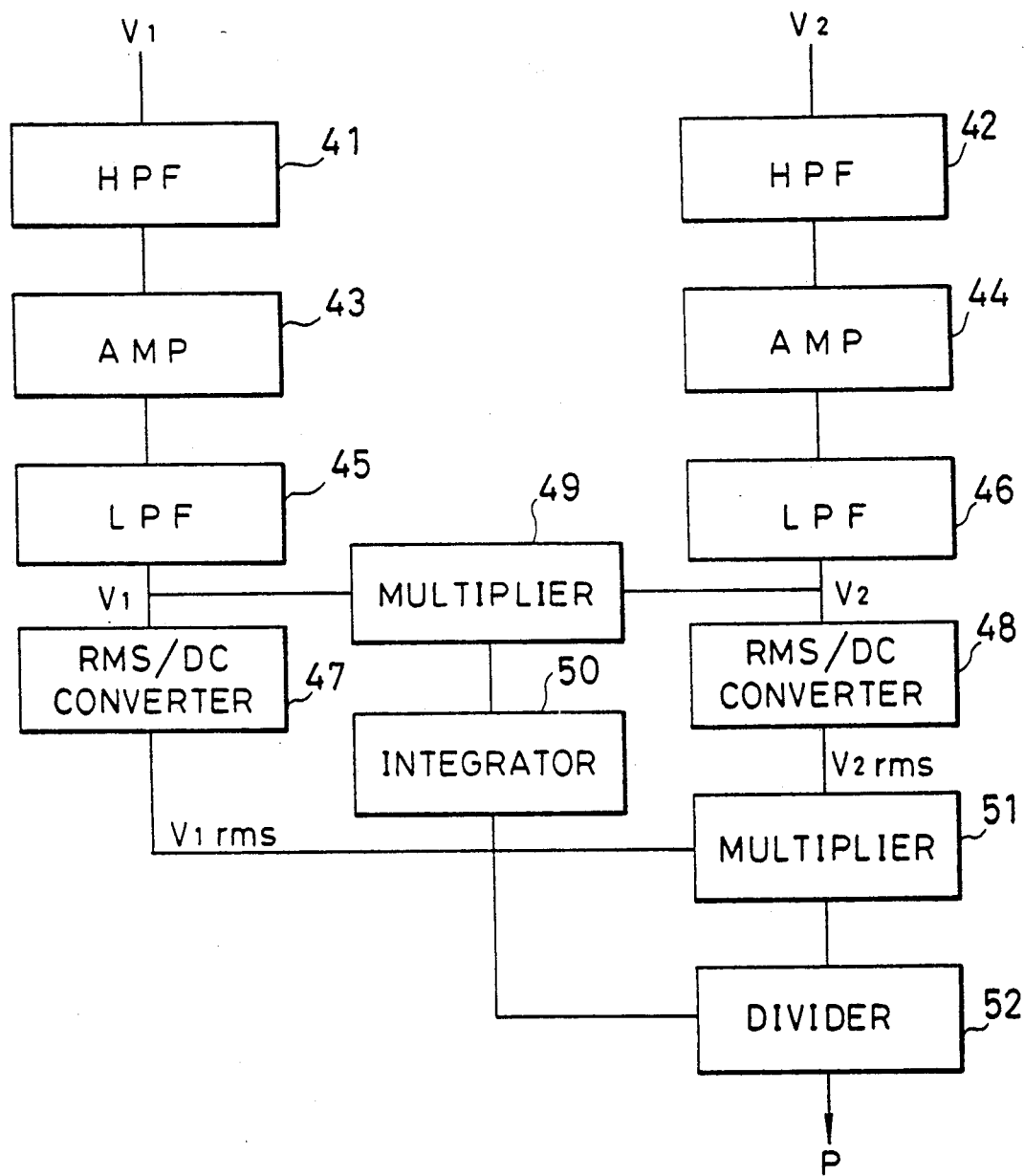
FIG. 5 is a block diagram showing a circuit for producing the correlation coefficient as its output.

In FIG. 5, the photoelectric converted signals $V_1$ and $V_2$ are discriminated of the DC components by high-pass filters (HPFs) 41 and 42, and then are amplified to a predetermined amplitude by amplifiers 43 and 44. In this case, the amplification factors have no effect on the correlation coefficient $\rho$, and hence the amplification factors can be adjusted so that sufficient signal-to-noise ratios can be achieved. The alternating signals thus obtained is deprived of harmful high frequency noises by the low-pass filters (LPFs) 45 and 46, and are fed to RMS-DC converters 47 and 48 as signals $V_1$ and $V_2$ so that the root-mean-square values of the respective signals $V_1$ and $V_2$ are calculated by the following operations.

$$V_{irms} = \sqrt{(1/T)\int V_i^2 dt} \qquad (57)$$

where $i = 1$ or $2$.

Furthermore, the signals $V_1$ and $V_2$ are converted to the covariance by the operation executed by a multiplier 49 and an integrator 50.

$$\overline{\tilde{V}_1 \cdot \tilde{V}_2} = (1/T)\int \tilde{V}_1 \cdot \tilde{V}_2 dt \qquad (58)$$

The effective values $V_{1rms}$ and $V_{2rms}$, and their covariance $\overline{\tilde{V}_1 \cdot \tilde{V}_2}$ are applied to a multiplier 51 and a divider 52 so that the correlation coefficient $\rho$ can be obtained by the following equation.

$$\rho = \overline{\tilde{V}_1 \cdot \tilde{V}_2} / (V_{1rms} \cdot V_{2rms}) \qquad (59)$$

Next, an example of practical measurements of the flocculation reaction by using the apparatus having the arrangement shown in FIGS. 1 and 3 will be described. The flocculation conditions were as follows: first, a 50 ppm kaolin suspension was prepared in a 2 liter stirred vessel; second, sodium hydroxide solution was added to the kaolin suspension so that the pH would become 7 after the addition of a flocculating agent; and third, the flocculating agent, aluminum sulfate of 3 ppm was added to the suspension in the strong stirred state. The stirring strength was adjusted by changing the number of revolutions of the stirring propellers, thus preparing the sample liquid of FIG. 1. The sampling liquid 7 was fed to the flow cell 6 by a pump not shown in FIG. 1, and the flow rate was kept constant during the experiment. The wavelengths used for measuring was specified as 255 nm and 830 nm to make the $(\alpha_1, \beta_1)$ and $(\alpha_2, \beta_1)$ diagonal dominating form: at 255 nm, absorptivity of aluminum sulfate hydrolysis product is large; and at 830 nm, absorption of kaolin is large.

Figure 6:
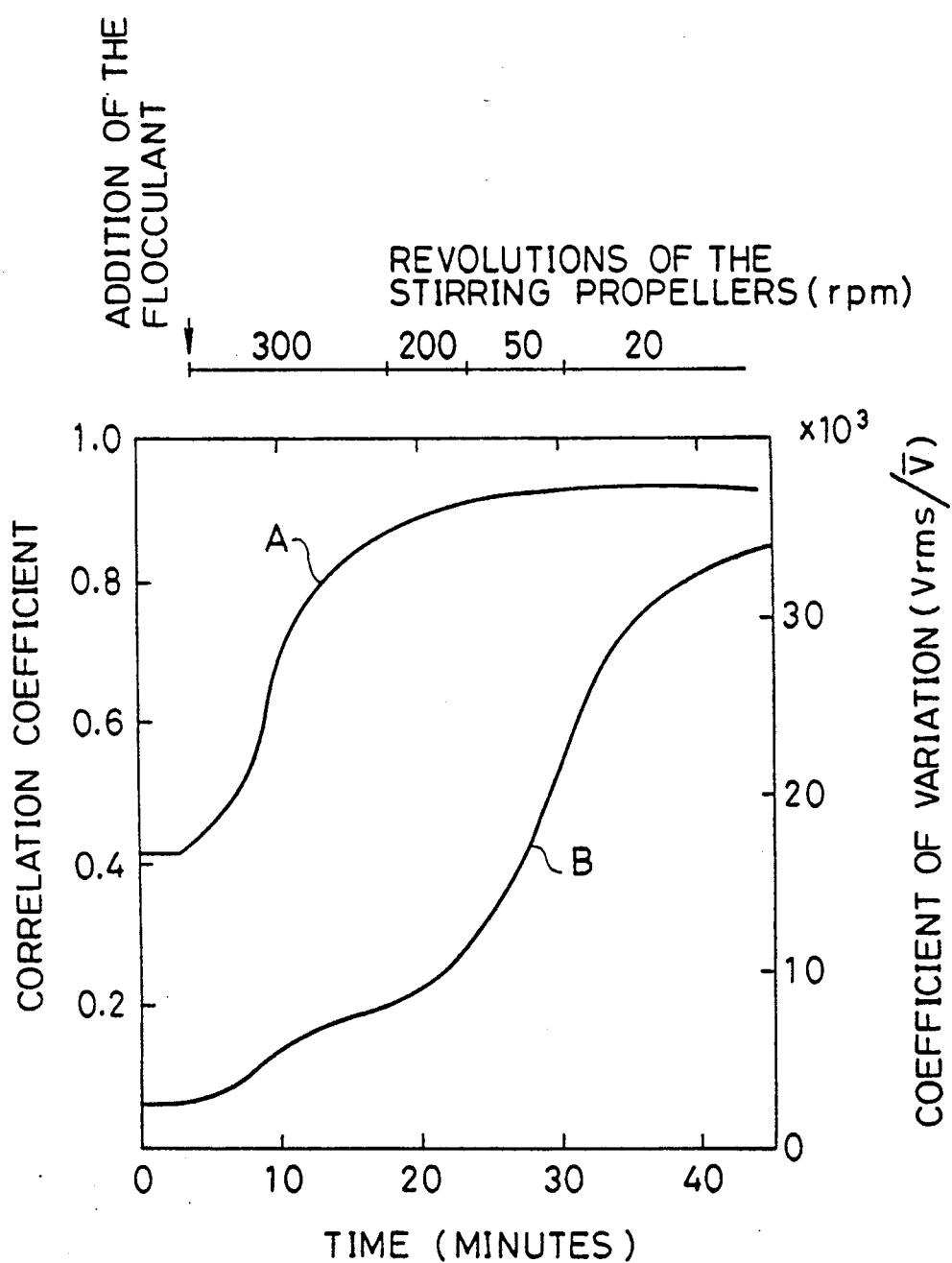
FIG. 6 is a graph illustrating the relationship between the elapsed time and the correlation coefficient, and between the elapsed time and the coefficient of variation when the flocculation reaction of the kaolin suspension is measured.

The results obtained is illustrated in FIG. 6. FIG. 6 is a diagram in which the correlation coefficient $\rho$ between the signals corresponding to the two wavelengths of the transmitted light signal, and the coefficient of variation $(V_{rms}/\overline{V})$ are plotted against the elapsed time: a curve A represents the correlation coefficient $\rho$, and a curve B represents the coefficient of variation $(V_{rms}/\overline{V})$ of the wavelength of 830 nm. Incidentally, the change in the number of revolutions of the stirring propellers from the time of addition of the flocculant is depicted in FIG. 6 with the elapsed time.

As described before, the coefficient of variation is identical to that measured by the conventional turbidity fluctuation method, and plays a role as an index of the average size of the flocs. As seen from the curve B, by reducing the stirring strength from a high-speed stirred state of 300–200 rpm to a slow-speed stirred state of 50–20 rpm, the average size of the flocs sharply increases. The correlation coefficient of the present invention, on the other hand, indicates the degree of progress of the flocculation reaction, and approaches 1 as the flocculation comes to an end. The curve A exhibits that the aggregation between the kaolin and the flocculating agent fast proceeds immediately after the addition of the flocculating agent, and nearly finishes by the high-speed stirring. Accordingly, growth of the flocs in the slow-speed stirred state is supposed to be due to collision and aggregation among the microflocs.

Next, the removed ratio of the dissolved components measured on the principle of the present invention will be described. This experiment is essentially identical to the previous experiment: as the sampling liquids, mixed liquids of various concentrations composed of kaolin and peatic colored water are used; as the flocculating agent, aluminum sulfate is used. Thus the flocculation processing is executed.

Figure 7:
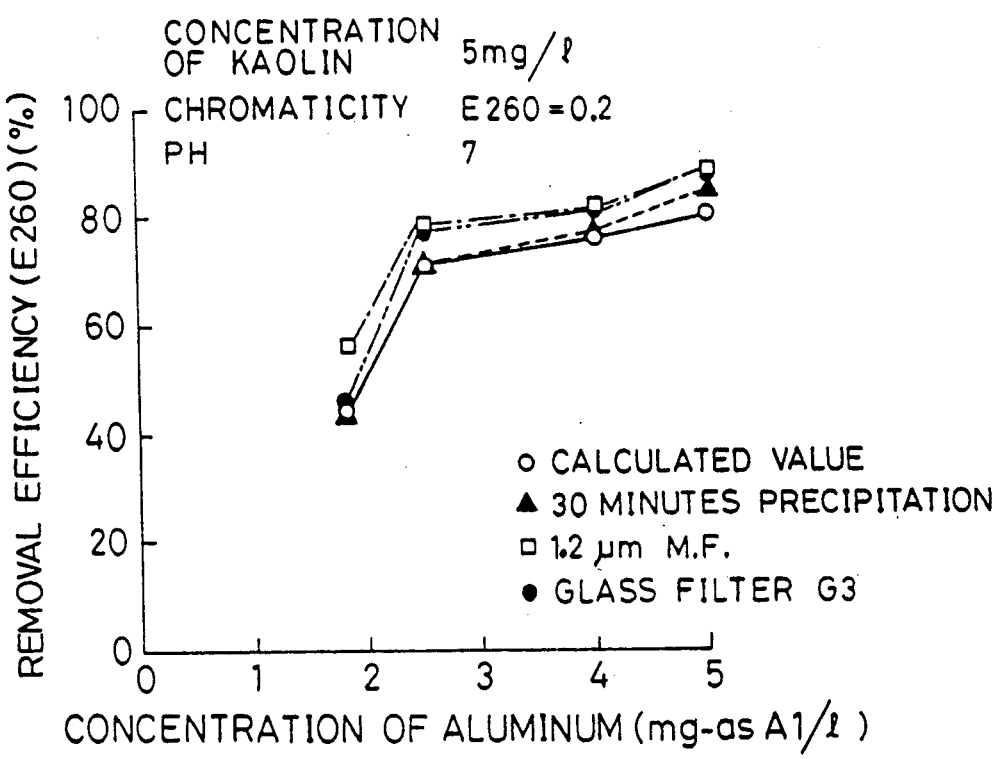
FIG. 7 is a graph illustrating the relationship between the concentration of flocculating agent (aluminum) and the removing ratio of chromaticity component, comprising the method of the present invention with a conventional method.

FIG. 7 is a diagram illustrating changes of the removal efficiency of color against changes of the injection ratio of the flocculating agent of kaolin with a concentration of 5 mg/liter, and chromaticity (260 nm absorbance) of 0.2. In FIG. 7, not only calculated values (open circle) by the method of the present invention are plotted, but also the following removal efficiency for comparison: the removed ratios of the supernatant liquid obtained after a 30-minute precipitation (closed triangle); the removal efficiency measured by the filtering method using 1.2 μm membrane filter (open square); and the removal efficiency measured by the filtering method using G3 glass filter (closed circle). FIG. 7 shows that the calculated values by the method of the present invention behave similarly to the values by the other methods: the removal efficiency of the present invention increases with the increase in the concentration of aluminum.

Figure 8:
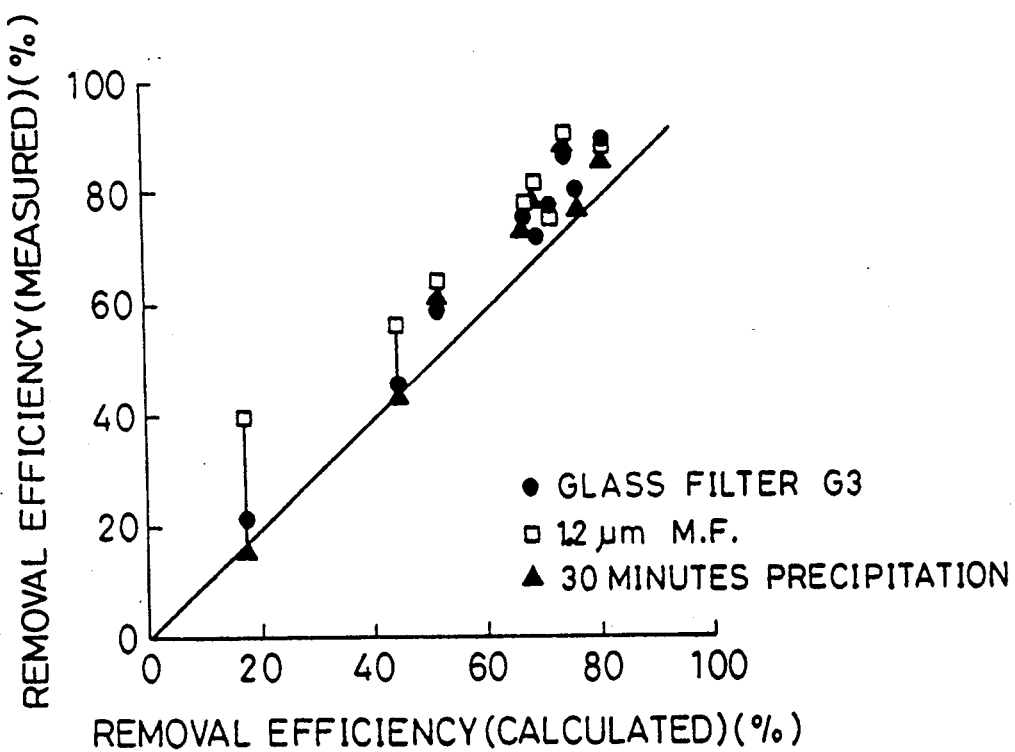
FIG. 8 is a graph illustrating the removal efficiency of color of the present invention and that of the conventional method.

FIG. 8 is a diagram comparing, under various conditions, the removal efficiency of the chromatic components of the present invention and other method mentioned above: the removal efficiency of the supernatant liquid obtained after a 30-minute precipitation (closed triangle); the removal efficiency measured by the filtering method using 1.2 μm membrane filter (open square); and the removal efficiency measured by the filtering method using G3 glass filter (closed circle). FIG. 8 shows that the method of the present invention has good correlation with the other methods. In particular, the method of the present invention agrees well with the method of 30-minute precipitation.

As described above, the present invention makes it possible to measure the flocculation process of a two-component suspension from the view point of progress of flocculation, and further to measure the sizes of flocs. Moreover, the present invention can be easily extended to measure the flocculation process of a multiple-component suspension by enabling the apparatus of the present invention to observe multiple wavelengths as shown in FIG. 2.

Using the apparatus and method of the present invention makes it possible to positively, effectively remove suspension components such as biometabolic organic substances which are precursors of trihalomethane, clay or the like in the flocculation process like water-purification process by controlling dosage or stirring.

APPENDIX 1

The method of the present invention detects the progress of the flocculation process in a sampling liquid as follows: first, the flow of the sampling liquid is illuminated by a beam of light; second, the transmitted beam of light is detected, and the component signals of the transmitted beam which correspond to the principal absorption wavelengths of respective suspended components in the sampling liquid are extracted; and third, the correlation coefficients between any two component signals are calculated on a real time basis. The principle of the present invention is described with regard to an example which uses a sample liquid including two types of suspended particles, and uses two wavelength light.

This Appendix 1 explains the relationship between the time serial correlation coefficient between the absorbances of the two wavelengths, and the concentrations of the respective components produced in the flocculation process of the two component system containing the components A and M, proves that the correlation coefficient is useful as an index indicating the progress of the flocculation process by the following equations (2)–(19), and considers the necessary conditions imposed on the selection of the wavelengths and on the components to be measured.

Equations (2)–(5) express the basic relations between the concentrations of respective components including the flocs A+M, and the absorbances and deviations of the absorbances at the respective wavelengths.

Equations (6)–(9) express the relations between the concentrations of the respective components and the basic statistics such as variances and covariances, which are calculated by using the measured absorbances of the wavelengths, on the basis of the equations (2)–(5).

Equations (10)–(15) prove that the mean values and variances of the transmitted light signals instead of the absorbances of the light signals can be used to express the equations (6)–(9) by using the approximation of the equation (12). This theoretically supports the operation for calculating the correlation coefficient between the two wavelengths by using simple analog circuitry.

The right-hand side of the equations (16)–(18) are for representing the correlation coefficient between the absorbances of the two wavelengths (or the substitute for the absorbances, which uses the transmitted light signals) by the concentrations of the components: the correlation coefficient can be expressed as follows:

correlation coefficient = right-hand side of
(18)/[right-hand side of (16)/right-hand side of
(17)]$^{\frac{1}{2}}$ by considering the equation, it is made clear that the correlation coefficient can be used as an index representing the flocculation process.

When $\alpha_1 \neq \alpha_2$, or $\beta_1 \neq \beta_2$, it is clear that the correlation coefficient is less than 1. In contrast, when the flocculation process successfully completed, the concentration $C_A$ of the component A and the concentration $C_M$ of the component M are both zero, and hence the numerator and denominator of the above equation expressing the correlation coefficient become equal. Thus, the correlation coefficient becomes one. In this case, the correlation coefficient approaches one with the decline in the concentrations $C_A$ and $C_M$.

Furthermore, when $\alpha_1 = \alpha_2$, and $\beta_1 = \beta_2$, the numerator and denominator of the above equation expressing the correlation coefficient become equal. Thus, the correlation coefficient takes a value of 1 regardless of the concentrations of the components.

From the above discussion, it is proved that the correlation coefficient can be used as an index indicating increasing flocs except for such a case in which the two components exhibit flat spectra independent of the wavelengths. This was confirmed by the experiment described within the embodiment.

In the description below, suffixes "1" and "2" correspond to the wavelengths $\lambda_1$ and $\lambda_2$, respectively. A suffix AM indicates that the component A in the flocs A+M is considered, and MA indicates that the component M in the flocs is considered. For example, $C_{AM}$ is a concentration of the component A in the flocs A+M, and $C_{MA}$ is a concentration of the component M in the flocs A+M. In addition, $\alpha$ designates the absorptivity of the component A, and $\beta$ indicates the absorptivity of the component M. C is a concentration and E is absorbance. Other characters used below will be described whenever they appear.

As described above, when the beam of light including two wavelength components $\lambda_1$ and $\lambda_2$ is transmitted through the suspension, the components of $\lambda_1$ and $\lambda_2$ are absorbed by the component A and the component M: in this case, the absorptivity of the components A for the wavelength $\lambda_1$ and $\lambda_2$ are $\alpha_1$ and $\alpha_2$, respectively; and the absorptivity of the component B for the wavelength $\lambda_1$ and $\lambda_2$ are $\beta_1$ and $\beta_2$, respectively. By using these symbols, the absorbances $E_1$ and $E_2$ of the suspension at the wavelengths $\lambda_1$ and $\lambda_2$ can be expressed by the following equations.

$$E_1 = \alpha_1 (C_A + C_{AM}) + \beta_1 (C_M + C_{MA}) \qquad (2)$$

$$E_2 = \alpha_2 (C_A + C_{AM}) + \beta_2 (C_M + C_{MA}) \qquad (3)$$

where
$C_A$: concentration of component A suspended in the liquid;
$C_{AM}$: concentration of component A in the flocs A+M;
$C_M$: concentration of component M suspended in the liquid;
$C_{MA}$: concentration of component M in the flocs A+M.

Here, fluctuations (deviations) $\widetilde{E}_1$ and $\widetilde{E}_2$ of the absorbances are considered which result from the localizations of concentrations of the respective components involved in the flocculation, and hence are expressed as follows:

$$\widetilde{E}_1 = \alpha_1 (\widetilde{C_A} + \widetilde{C_{AM}}) + \beta_1 (\widetilde{C_M} + \widetilde{C_{MA}}) \qquad (4)$$

$$\widetilde{E}_2 = \alpha_2 (\widetilde{C_A} + \widetilde{C_{AM}}) + \beta_2 (\widetilde{C_M} + \widetilde{C_{MA}}) \qquad (5)$$

where ~ indicates a deviation.

Accordingly, the variances (the square of the standard deviation) $\overline{\widetilde{E_1}^2}$ and $\overline{\widetilde{E_2}^2}$ can be expressed by the following equations considering that the components A and M are independent, that the concentration $C_{AM}$ of the component A in the flocs A+M and the concentration $C_{MA}$ of the component M in the flocs A+M are dependent, and that the correlation coefficient between $C_{AM}$ and $C_{MA}$ is 1.

$$\overline{\widetilde{E_1}^2} = \alpha_1^2 (\overline{\widetilde{C_A}^2} + \overline{\widetilde{C_{AM}}^2}) + \beta_1^2 (\overline{\widetilde{C_M}^2} + \overline{\widetilde{C_{MA}}^2}) + \qquad (6)$$

$$2\alpha_1 \beta_1 \sqrt{\overline{\widetilde{C_{AM}}^2} \cdot \overline{\widetilde{C_{MA}}^2}}$$

$$\overline{\widetilde{E_2}^2} = \alpha_2^2 (\overline{\widetilde{C_A}^2} + \overline{\widetilde{C_{AM}}^2}) + \beta_2^2 (\overline{\widetilde{C_M}^2} + \overline{\widetilde{C_{MA}}^2}) + \qquad (7)$$

$$2\alpha_2 \beta_2 \sqrt{\overline{\widetilde{C_{AM}}^2} \cdot \overline{\widetilde{C_{MA}}^2}}$$

where the overline — represents a mean value, which is used hereinafter.

The correlation coefficient $\rho$ between $E_1$ and $E_2$ is expressed as $$\rho = \overline{\widetilde{E_1} \cdot \widetilde{E_2}} / \sqrt{\overline{\widetilde{E_1}^2} \cdot \overline{\widetilde{E_2}^2}} \qquad (8)$$

and the covariance $\overline{\tilde{E}_1 \cdot \tilde{E}_2}$ is given by the following equation.

$$\overline{\tilde{E}_1 \cdot \tilde{E}_2} = \alpha_1 \alpha_2 (\overline{\widetilde{C_A}^2} + \overline{\widetilde{C_{AM}}^2}) + \beta_1 \beta_2 (\overline{\widetilde{C_M}^2} + \overline{\widetilde{C_{MA}}^2}) + \quad (9)$$

$$(\alpha_1\beta_2 + \alpha_2\beta_1) \sqrt{\overline{\widetilde{C_{AM}}^2} \cdot \overline{\widetilde{C_{MA}}^2}}$$

Here, by representing the photoelectric conversion output of the transmitted light by V, and the photoelectric conversion output of pure water without suspensoid by $V_0$, the following is obtained.

$$E = l_n (V_0/V) \quad (10)$$

$$\overline{E} = l_n (V_0/\overline{V}) \quad (11)$$

Then, $$\begin{aligned}
\tilde{E} &= E - \overline{E} \\
&= l_n (\overline{V}/V) \\
&= l_n [\overline{V}/(\overline{V} + \tilde{V})] \\
&= -l_n (1 + \tilde{V}/\overline{V}) \\
&\approx - \tilde{V}/\overline{V}
\end{aligned} \quad (12)$$

and $$\begin{aligned}
\overline{\tilde{E}^2} &= \overline{\tilde{V}^2} - \overline{V}^2 \\
&= V_{rms}^2/\overline{V}^2 \\
&= (V_{rms}/\overline{V}^2)
\end{aligned} \quad (13)$$

$$\sqrt{\overline{\tilde{E}^2}} = V_{rms}/\overline{V} \quad (14)$$

$$\overline{\tilde{E}_1 \cdot \tilde{E}_2} = \overline{\tilde{V}_1 \cdot \tilde{V}_2}/(\overline{V}_1 \cdot \overline{V}_2) \quad (15)$$

where rms means root mean square.

The insertion of the equations (14) and (15) into the equations (6), (7) and (9) yields $$(V_{1rms}/\overline{V}_1)^2 = \alpha_1^2 (\overline{\widetilde{C_A}^2} + \overline{\widetilde{C_{AM}}^2}) + \beta_1^2 (\overline{\widetilde{C_M}^2} + \overline{\widetilde{C_{MA}}^2}) + \quad (16)$$

$$2\alpha_1\beta_1 \sqrt{\overline{\widetilde{C_{AM}}^2} \cdot \overline{\widetilde{C_{MA}}^2}}$$

$$(V_{2rms}/\overline{V}_2)^2 = \alpha_2^2 (\overline{\widetilde{C_A}^2} + \overline{\widetilde{C_{AM}}^2}) + \beta_2^2 (\overline{\widetilde{C_M}^2} + \overline{\widetilde{C_{MA}}^2}) + \quad (17)$$

$$2\alpha_2\beta_2 \sqrt{\overline{\widetilde{C_{AM}}^2} \cdot \overline{\widetilde{C_{MA}}^2}}$$

$$\overline{\tilde{V}_1 \cdot \tilde{V}_2}/(\overline{V}_1 \cdot \overline{V}_2) = \alpha_1\alpha_2 (\overline{\widetilde{C_A}^2} + \overline{\widetilde{C_{AM}}^2}) + \beta_1\beta_2 (\overline{\widetilde{C_M}^2} + \overline{\widetilde{C_{MA}}^2}) + \quad (18)$$

$$(\alpha_1\beta_2 + \alpha_2\beta_1) \sqrt{\overline{\widetilde{C_{AM}}^2} \cdot \overline{\widetilde{C_{MA}}^2}}$$

$$\begin{aligned}
\rho &= \overline{\tilde{E}_1 \cdot \tilde{E}_2}/\sqrt{\overline{\tilde{E}_1^2} \cdot \overline{\tilde{E}_2^2}} \\
&= \overline{\tilde{V}_1 \cdot \tilde{V}_2}/(V_{1rms} \cdot V_{2rms})
\end{aligned} \quad (19)$$

From the right-hand sides of the equations (16), (17) and (18), it follows that the correlation coefficient $\rho$ is dependent on the concentrations of components in the flocs, and on the concentrations of components in the liquid except when $\alpha_1 = \alpha_2$ and $\beta_1 = \beta_2$, that is, except when the component signals of the transmitted light corresponding to the components A and M have no wavelength dependence. More specifically, when all the components individually exist in the suspension, the events that the respective components exist in the light beam are independent, and hence the covariances corresponding to these events are less than the products of the respective standard deviations corresponding thereto. Thus, the correlation coefficients are less than 1. On the other hand, when the components A and M have completely flocculated, the variations of the component signals of the transmitted light are synchronized with each other, and further, the composition ratios of the respective components of the individual flocs become nearly constant. Accordingly, when the matrix $$\begin{pmatrix} \alpha_1 & \beta_1 \\ \alpha_2 & \beta_2 \end{pmatrix}$$

is specified so that it takes a diagonally dominating form, the correlation coefficients can be made to take a value of 1 at flocculation, and a value of approximately 0 at non-flocculation.

APPENDIX 2

The present invention makes it possible to calculate the absorbance of the uncoagulated dissolved component in the in-line processing without carrying out preliminary processing to the suspension, by measuring the fluctuation of absorbance caused by the suspended particles when the two wavelengths of light pass through the flow of the suspension. In this appendix 2, the validity of the calculation method of the concentration of the uncoagulated dissolved component is theoretically proved in the process in which equation (1) is derived from the following equations (20)–(48).

The equations are developed so that a component of the absorbance of the wavelength $\lambda_2$, namely, the absorbance that is caused by the suspended particles, is expressed by measurable quantities, and by subtracting this absorbance from the total absorbance of the wavelength $\lambda_2$, the absorbance of the uncoagulated dissolved component can be obtained.

The first stage of the development of equations [in connection with equations (20)–(24)], shows that the number of the suspended particles passing through the light beam can be expressed by the mean values and standard deviations of the absorbances, by using the fact that the probability distribution, in a specific space of randomly dispersed particles in a space follows the Poisson distribution.

The second stage of the development of the equations [in connection with equations (25)–(27)], shows that the mean number of the suspended particles which are present in the light beam and are observed by the light of wavelength $\lambda_2$, can be expressed by the total sum of the numbers of respective components.

The third stage of the development of the equations [in connection with equations (28)–(41)] shows the changing process of equations, wherein the equation (27) of the second stage expressing the mean number of the suspended particles is replaced with the means and standard deviations of the absorbances corresponding to respective terms of equation (27) [equation (28)] so that the right-hand side of equation (28) can be immediately calculated from measurable values. The resultant equation is (41), which is a quadratic with regard to $E_2$ because the other variables can be directly measurable or calculable. Equation (42) is a root of equation (41), which is subtracted from the total absorbance $E_{2obs}$ of the wavelength $\lambda_2$, thereby yielding the absorbance of the uncoagulated dissolved component at the wavelength $\lambda_2$ [equation (44)], which is the end of the development of the equations.

Equations (45)–(47) show that the following two approaches give the same result with regard to the absorbance of the dissolved component at the time the flocculation process has completed. One approach calculates the absorbance from the balance of the number of the suspended particles. The other approach calculates the absorbance from the correlation coefficient of the absorbances of the two wavelengths, thereby asserting the validity of equation (44).

Next, the equation (A) expressing the absorbance of dissolved components which have not been flocculated will be explained. Here, the above-mentioned two wavelengths $\lambda_1$ and $\lambda_2$ are selected so that the component light of wavelength $\lambda_1$ is absorbed by suspended components, and the component light of wavelength $\lambda_2$ is absorbed by the suspended components and the dissolved components. As is generally known, the number of the suspended particles passing through the light beam varies in accordance with the Poisson distribution. Assuming that the number concentration of particles in the suspension is C, and the number of particles in the suspension is n, C is expressed by $$C = k\,n \tag{20}$$

Further, assuming that the standard deviation of the variation of the number concentration C is Cr, the following equations are obtained.

$$C_m = k\,\nu \tag{21}$$

$$C_r = k\,\sigma^{\frac{1}{2}} = k\,\nu^{\frac{1}{2}} \tag{22}$$

where
 $\sigma$: variance of the number of particles in the suspension in the light beam;
 $\nu$ is the average number of the particles in the suspension; and
 Cm is the average value of the number concentration.
It follows from the equations (21) and (22) that $$C_r/C_m = \nu^{\frac{1}{2}} \tag{23}$$

Since the absorbance is directly proportional to the concentration, it follows the $$E_r/\overline{E} = \nu^{\frac{1}{2}} \tag{24}$$

Here, the average number $\nu_2$ of the suspended particles measured by the light of wavelength $\lambda_2$ can be expressed by $$\nu_2 = \nu_{21} + \nu_{22} \tag{25}$$

where
 $\nu_{21}$ is the average number of heterofloc (A+B+X) composed of suspended components A and components B having flocculant X;
 $\nu_{22}$ is the average number of floc (B+X) composed of dissolved components B and flocculant X;
 $\nu_2$ is the average number of flocs [(A+B+X)+(B+X)] absorbing the light of wavelength $\lambda_2$; and
 $\nu_1$ is the average number of suspended components A.
Furthermore, since the average number of suspended particles measured by the light of wavelength $\lambda_1$ and $\lambda_2$ will agree if the hetero-flocculation of the suspension components A and dissolved components B that are captured by flocculant X has been completed, it follows that $$\nu_{21} = \nu_1 \tag{26}$$

and hence the equation (25) can be written in the form $$\nu_2 = \nu_1 + \nu_{22} \tag{27}$$

Assuming that the absorption (scattering) cross-sectional areas of the hetero-flocs (A+B+X) and flocs (B+X) are equal, the equation (27) can be rewritten as follows by using the absorbances given by the relation of the equation (24)

$$(\overline{E_2}/E_{r2})^2 = (\overline{E_1}/E_{r1})^2 + (\overline{E_{22}}/E_{r22})^2 \tag{28}$$

The correlation coefficient $\rho_{12}$ between the absorbances of the light of wavelengths $\lambda_1$ and $\lambda_2$ is expressed as the following equation.

$$\rho_{12} = \overline{\overline{E_1}\cdot\overline{E_2}}/(E_{r1}\cdot E_{r2}) \tag{29}$$

The covariance $\overline{\overline{E_1}\cdot\overline{E_2}}$ is expressed by the following equation.

$$\overline{\overline{E_1}\cdot\overline{E_2}} = \overline{\overline{E_1}\cdot(\overline{E_{21}}+\overline{E_{22}})} = \overline{\overline{E_1}\cdot\overline{E_{21}}} \tag{30}$$

where $E_1$ and $E_{22}$ are independent events. Accordingly, the equation (29) can be written in the form $$\rho_{12} = \overline{\overline{E_1}\cdot\overline{E_{21}}}/(E_{r1}\cdot E_{r2}) \tag{31}$$

In addition, since the fluctuations $E_1$ and $E_{21}$ of the absorbances are dependent variables, the correlation coefficient between these variables is 1, and hence the following equation is obtained.

$$\overline{\overline{E_1}\cdot\overline{E_{21}}}/(E_{r1}\cdot E_{r2}) = 1 \tag{32}$$

From the equations (31) and (32), it follows that $$E_{r21} = \rho_{12}\cdot E_{r2} \tag{33}$$

The variance $E_{r2}$ of the absorbance measured by the light of wavelength $\lambda_2$ is expressed by the following equation.

$$E_{r2}^2 = E_{r21}^2 + E_{r22}^2 \tag{34}$$

The insertion of (33) in (34) yields $$E_{r22} = \sqrt{1 - \rho_{12}^2}\cdot E_{r2} \tag{35}$$

On the other hand, the average value $\overline{E}_2$ of the absorbance of the flocs measured by the light of wavelength $\lambda_2$ is expressed by the following equation.

$$\overline{E_2} = \overline{E_{21}} + \overline{E_{22}} \tag{36}$$

The second term of the right-hand side of the equation (28) is expressed by the following equation using the relation of the equation (36)

$$(\overline{E_2}/E_{r2})^2 \approx (\overline{E_1}/E_{r1})^2 + [(\overline{E_2} - \overline{E_{21}})/E_{r2} \cdot \sqrt{1 - \rho_{12}^2}]^2 \quad (37)$$

Furthermore, from the relation of the equation (26)

$$\overline{E_{21}}/E_{r21} = \overline{E_1}/E_{r1} \quad (38)$$

and hence $$\overline{E_{21}} = \overline{E_1} \cdot E_{r21}/E_{r1} \quad (39)$$

In addition, from the equation (33)

$$\overline{E_{21}} = \rho_{12} \cdot \overline{E_1} \cdot E_{r2}/E_{r1} \quad (40)$$

Accordingly, the equation (37) can be written in the form $$(\overline{E_2}/E_{r2})^2 = (\overline{E_1}/E_{r1})^2 + \quad (41)$$

$$[(\overline{E_2} - \rho_{12} \cdot \overline{E_1} \cdot E_{r2}/E_{r1})/E_{r2} \cdot \sqrt{1 - \rho_{12}^2}]^2$$

This equation (41) can be considered as a quadratic equation with regard to the unknown $\overline{E_2}$ because all the variances except for the $\overline{E_2}$ (the average value of the absorbance of the floc in the absorbance of the light of wavelength $\lambda_2$) are measurable statistics. The positive root of the equation (41) is expressed as the following equation (the negative root is ignored because it has no physical meaning):

$$\overline{E_2} = \overline{E_1} \cdot E_{r2}/(\rho_{12} \cdot E_{r1}) \quad (42)$$

On the other hand, since the average value $\overline{E_{2obs}}$ of the absorbance measured by the light of wavelength $\lambda_2$, it follows that $$\overline{E_{2obs}} = E_2' + \overline{E_2} \quad (43)$$

and hence the absorbance of the dissolved components that have not yet flocculated is given by $$E_2' = \overline{E_{2obs}} - \overline{E_1} \cdot E_{r2}/(\rho_{12} \cdot E_{r1}) \quad (44)$$

When the floc (B+X) formed by the dissolved components B and flocculant X cannot exist, the equation (28) is written in the form of $$(\overline{E_2}/E_{r2})^2 = (\overline{E_1}/E_{r1})^2 \quad (45)$$

or $$\overline{E_2} = \overline{E_1} \cdot E_{r2}/(E_{r1}) \quad (46)$$

and hence the following equation can be obtained.

$$E_2' = \overline{E_{2obs}} - \overline{E_1} \cdot E_{r2}/E_{r1} \quad (47)$$

This equation agrees with the equation obtained by supposing that the correlation coefficient between the absorbances of two wavelengths of light is 1, that is, the two wavelengths of light measure the same floc. Accordingly, the equation (44) [i.e., the equation (1) mentioned before] can be considered as a strict solution.

By using thus determined absorbance $E_2'$ of the dissolved components that have not yet been flocculated, and the absorbance $\overline{E_2}°$ of the initial dissolved components before a flocculating agent is put into the suspension, the removal efficiency P of the dissolved components resulting from the flocculation reaction can be calculated by the following equation.

$$P = 100 \times E_2'/\overline{E_2}° \quad (48)$$

Although specific embodiments of a method and apparatus for detecting flocculation process of components in a liquid constructed in accordance with the present invention have been disclosed, it is not intended that the invention be restricted to either the specific configurations or the uses disclosed herein. Modifications may be made in a manner obvious to those skilled in the art. Accordingly, it is intended that the invention be limited only by the scope of the appended claims.

What is claimed is:

1. A method for detecting progress of a flocculation process of a plurality of components in a sample liquid, the flocculation process being produced by adding a flocculant into the sample liquid including at least a suspended component and a dissolved component, comprising the steps of:

simultaneously irradiating on a single optical axis a flow of the sample liquid with a beam including at least a first wavelength component and a second wavelength component, the first wavelength component having a different wavelength than the second wavelength component;

converting said beam after transmission through said sample liquid into electric signals corresponding to the first and second wavelength components;

calculating from said electric signals the intensities, mean values, standard deviations and coefficients of variation of absorbances of the first and second wavelength components;

calculating correlation coefficients between the intensities of the first and second wavelength components of the transmitted beam;

selecting the wavelength of the first wavelength component so as to be absorbed only by the suspended component and selecting the wavelength of the second wavelength component so as to be absorbed by both the suspended component and the dissolved component including the flocculant; and said calculating step further comprising the substeps of:

calculating a mean value $\overline{E_1}$ of absorbance of the first wavelength component;

calculating a standard deviation $E_{r1}$ of the absorbance of the first wavelength component;

calculating a mean value $\overline{E_2}$ of absorbance of the second wavelength component;

calculating a standard deviation $E_{r2}$ of the absorbance of the second wavelength component;

calculating a time serial correlation coefficient $\rho_{12}$ between the absorbances of the first and second wavelength components; and calculating absorbance $E_2'$ corresponding to an amount of uncoagulated dissolved component which is uniformly contained in the sample liquid without having been adsorbed by particles in the sample liquid and consequently corresponding to progress of the flocculation process, by using the following equation and the values $\overline{E_1}$, $E_{r1}$, $\overline{E_2}$, $E_{r2}$, and $\rho_{12}$ $$E_2' = \overline{E_2} - \frac{\overline{E_1}}{\rho_{12}} \cdot \frac{E_{r2}}{E_{r1}}.$$

2. An apparatus for detecting the progress of a flocculation process of a plurality of components in a sample liquid, the flocculation process being produced by adding a flocculant into the sample liquid containing at least a suspended component and a dissolved component, comprising:

a light source for emitting a beam of light including a plurality of wavelength components each having a different wavelength;

a flow cell through which the sample liquid flows;

first optical means for simultaneously transmitting on a single optical axis a portion of the beam of light through said flow cell yielding a transmitted beam of light;

photoelectric converting means for receiving and converting the transmitted beam of light into electric signals each corresponding to a respective one of the wavelength components;

calculating means for calculating from the electric signals intensities, mean values, standard deviations and coefficients of variation of absorbances of the plurality of wavelength components, and for calculating correlation coefficients between the intensities of the plurality of wavelength components of the transmitted beam of light; and means for selecting the wavelength of a wavelength component of the plurality of wavelengths so as to be absorbed only by the suspended component and selecting the wavelength of a second wavelength component of the plurality of wavelengths so as to be absorbed by both the suspended component and the dissolved component including the flocculant, said calculating means including means for calculating a mean value $\overline{E_1}$ of absorbance of the first wavelength component, a standard deviation $E_{r1}$ of the absorbance of the first wavelength component, a mean value $\overline{E_2}$ of absorbance of the second wavelength component, a standard deviation $E_{r2}$ of the absorbance of the second wavelength component, a time serial correlation coefficient $\rho_{12}$ between the absorbances of the first and second wavelength components, and absorbance $E_2'$ corresponding to an amount of uncoagulated dissolved component which is uniformly contained in the sample liquid without having been adsorbed by particles in the sample liquid and consequently corresponding to progress of the flocculation process, by using the following equation and the values $\overline{E_1}$, $E_{r1}$, $\overline{E_2}$, $E_{r2}$, and $\rho_{12}$ $$E_2' = \overline{E_2} - \frac{\overline{E_1}}{\rho_{12}} \cdot \frac{E_{r2}}{E_{r1}}.$$

3. A method for detecting progress of a flocculation process of a plurality of components in a sample liquid, the flocculation process being produced by adding a flocculant into the sample liquid including at least a suspended component and a dissolved component, comprising the steps of:

generating a light beam including at least a first wavelength component and a second wavelength component, the first wavelength component having a different wavelength than the second wavelength component;

simultaneously irradiating on a single optical axis a flow of the sample liquid with the beam;

converting said beam after transmission through said sample liquid into first and second electrical signals corresponding to said first and second wavelength components respectively;

calculating from said first and second electrical signals the intensities of said first and second wavelength components;

calculating correlation coefficients between the intensities of said first and second wavelength components of the transmitted beam; and selecting the wavelength of the first wavelength component so as to be absorbed only by the suspended component and selecting the wavelength of the second wavelength component so as to be absorbed by both the suspended component and the dissolved component including the flocculant; and said calculating steps further comprising the substeps of:

calculating a mean value $\overline{E_1}$ of absorbance of the first wavelength component;

calculating a standard deviation $E_{r1}$ of the absorbance of the first wavelength component;

calculating a mean value $\overline{E_2}$ of absorbance of the second wavelength component;

calculating a standard deviation $E_{r2}$ of the absorbance of the second wavelength component;

calculating a time serial correlation coefficient $\rho_{12}$ between the absorbances of the first and second wavelength components; and calculating absorbance $E_2'$ corresponding to an amount of uncoagulated dissolved component which is uniformly contained in the sample liquid without having been adsorbed by particles in the sample liquid and consequently corresponding to progress of the flocculation process, by using the following equation and the values $\overline{E_1}$, $E_{r1}$, $\overline{E_2}$, $E_{r2}$, and $\rho_{12}$ $$E_2' = \overline{E_2} - \frac{\overline{E_1}}{\rho_{12}} \cdot \frac{E_{r2}}{E_{r1}}.$$

* * * * *